(12) United States Patent
Dreyfuss

(10) Patent No.: US 8,162,947 B2
(45) Date of Patent: Apr. 24, 2012

(54) DOME SHAPED IMPLANT AND INSERTER

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1057 days.

(21) Appl. No.: 12/061,396

(22) Filed: Apr. 2, 2008

(65) Prior Publication Data

US 2008/0249577 A1  Oct. 9, 2008

Related U.S. Application Data

(60) Provisional application No. 60/910,073, filed on Apr. 4, 2007.

(51) Int. Cl.
*A61F 2/46* (2006.01)

(52) U.S. Cl. .................................... 606/86 R

(58) Field of Classification Search .............. 606/99, 606/104; 411/402, 403; 81/176.2, 176.3, 81/442–449
See application file for complete search history.

(56) References Cited

U.S. PATENT DOCUMENTS

| 66,585 | A | * | 7/1867 | Harvey | 81/443 |
| 3,379,231 | A | * | 4/1968 | Gallo, Sr. | 81/455 |
| 5,147,386 | A | | 9/1992 | Carignan et al. | |
| 6,189,422 | B1 | * | 2/2001 | Stihl | 81/452 |
| 6,520,964 | B2 | * | 2/2003 | Tallarida et al. | 606/71 |
| 7,261,716 | B2 | * | 8/2007 | Strobel et al. | 606/314 |

FOREIGN PATENT DOCUMENTS

| DE | 76 01 139 | 5/1976 |
| FR | 2 395 011 | 1/1979 |
| FR | 2 663 838 | 1/1992 |

\* cited by examiner

*Primary Examiner* — Anu Ramana
(74) *Attorney, Agent, or Firm* — Dickstein Shapiro LLP

(57) ABSTRACT

An implant for resurfacing a joint and a driver for the implant. The inserter attaches to the head of the implant. The inserter is designed to facilitate the handling and insertion of an implant at a surgical site. The inserter is provided with a plurality of arms that securely engage a plurality of indents on the edge or periphery of the implant.

5 Claims, 8 Drawing Sheets

DOME SHAPED IMPLANT AND INSERTER

CROSS REFERENCE TO RELATED APPLICATIONS

This application claims the benefit of U.S. Provisional Application Ser. No. 60/910,073 filed on Apr. 4, 2007, the entire disclosure of which is incorporated by reference in its entirety herein.

FIELD OF THE INVENTION

The present invention relates to a dome shaped implant for joint resurfacing and an inserter for the implant.

BACKGROUND OF THE INVENTION

When a bearing surface of a joint becomes damaged, one solution is to replace the damaged surface with an implant having a hemispherical surface that matches the contour of the damaged cartilage of the joint. Insertion of these implants, is typically problematic as it is difficult to handle such fixation devices within the joint capsule (during arthroscopic surgery, for example) where visibility and access to the structures of the joint is minimal. It is also difficult to precisely position such fixation devices at the arthroscopic site.

Accordingly, a need exists for a surgical implant and inserter that is configured to facilitate handling of the implant within a joint capsule, for example the knee capsule or the shoulder joint, during surgical reconstruction. A need also exists for a surgical implant and inserter that is stable during surgery and that allows for precise positioning of the implant during insertion and fixation.

SUMMARY OF THE INVENTION

The present invention provides an implant/inserter assembly designed to facilitate the handling and subsequent insertion of an implant at a surgical site. The inserter is provided with a plurality of arms that securely engage a plurality of indents on the edge or periphery of the implant.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

Figure 1:
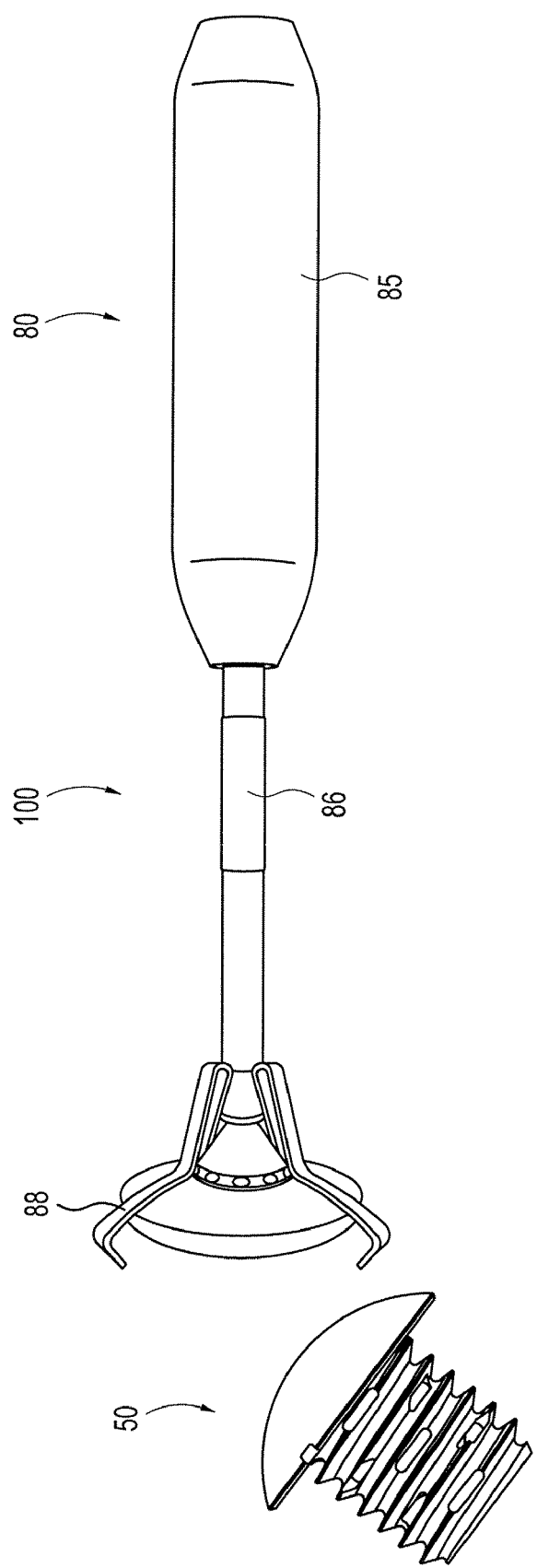
FIG. 1 illustrates a perspective view of an implant/inserter assembly of the present invention, in a detached state.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides a dome shaped implant and an inserter that is configured to allow improved handling of the implant within a joint capsule, for example the knee capsule or the shoulder joint, during surgical reconstruction.

The implant of the present invention is designed to be securely engaged by a corresponding inserter or driver. The implant is preferably provided with a dome or eclipse-like head having a plurality of indents on the periphery of the head. The plurality of indents are configured to be engaged by arms (tabs) of a corresponding inserter instrument.

The present invention also provides an inserter designed to increase the handling and subsequent insertion of the implant at a surgical site. The inserter is provided with a plurality of arms that securely engage a plurality of indents on the edge or periphery of the implant. In an exemplary embodiment, the arms of the inserter attach to the implant by sliding back the shaft of the inserter. Alternatively, the arms of the inserter detach from the implant by sliding the shaft forward (with open arms).

The present invention also provides a method of conducting surgery by: (i) forming a socket at a surgical repair site; (ii) providing an implant/inserter assembly in the vicinity of the surgical repair site; and (iii) securing the implant at least partially within the socket.

Referring now to the drawings, where like elements are designated by like reference numerals, FIGS. 1-8 illustrate various components of an implant/inserter assembly 100 of the present invention. The implant/inserter assembly 100 allows improved handling of the implant within a joint capsule, for example the knee capsule or the shoulder joint, during surgical reconstruction.

Figure 2:
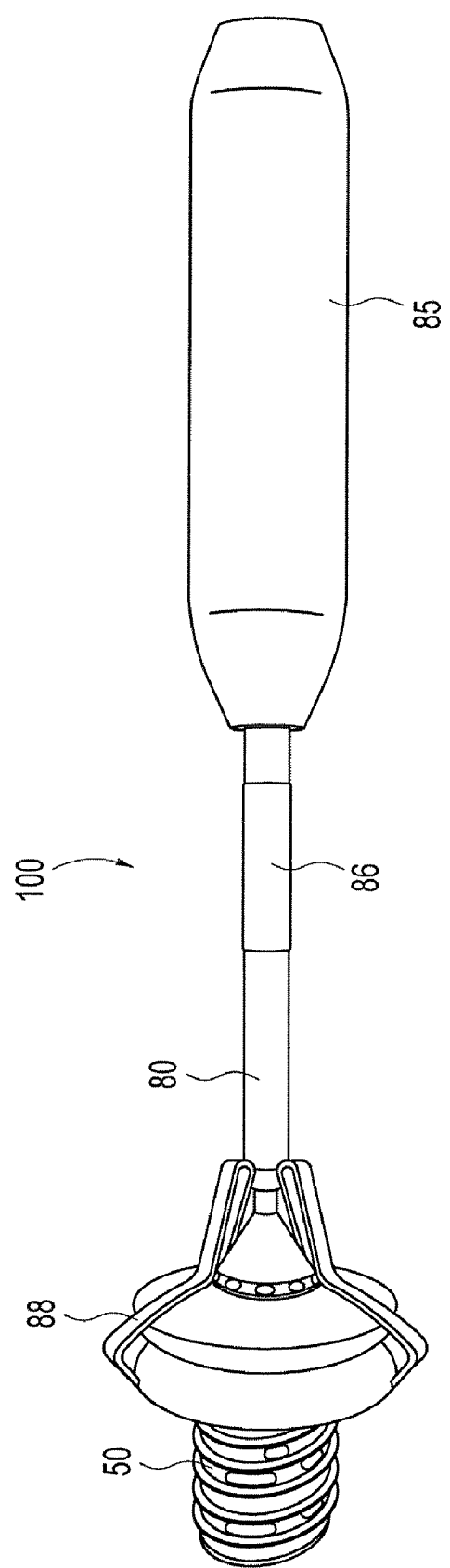
FIG. 2 illustrates a perspective view of an implant/inserter assembly of the present invention, in an attached state.
Figure 3:
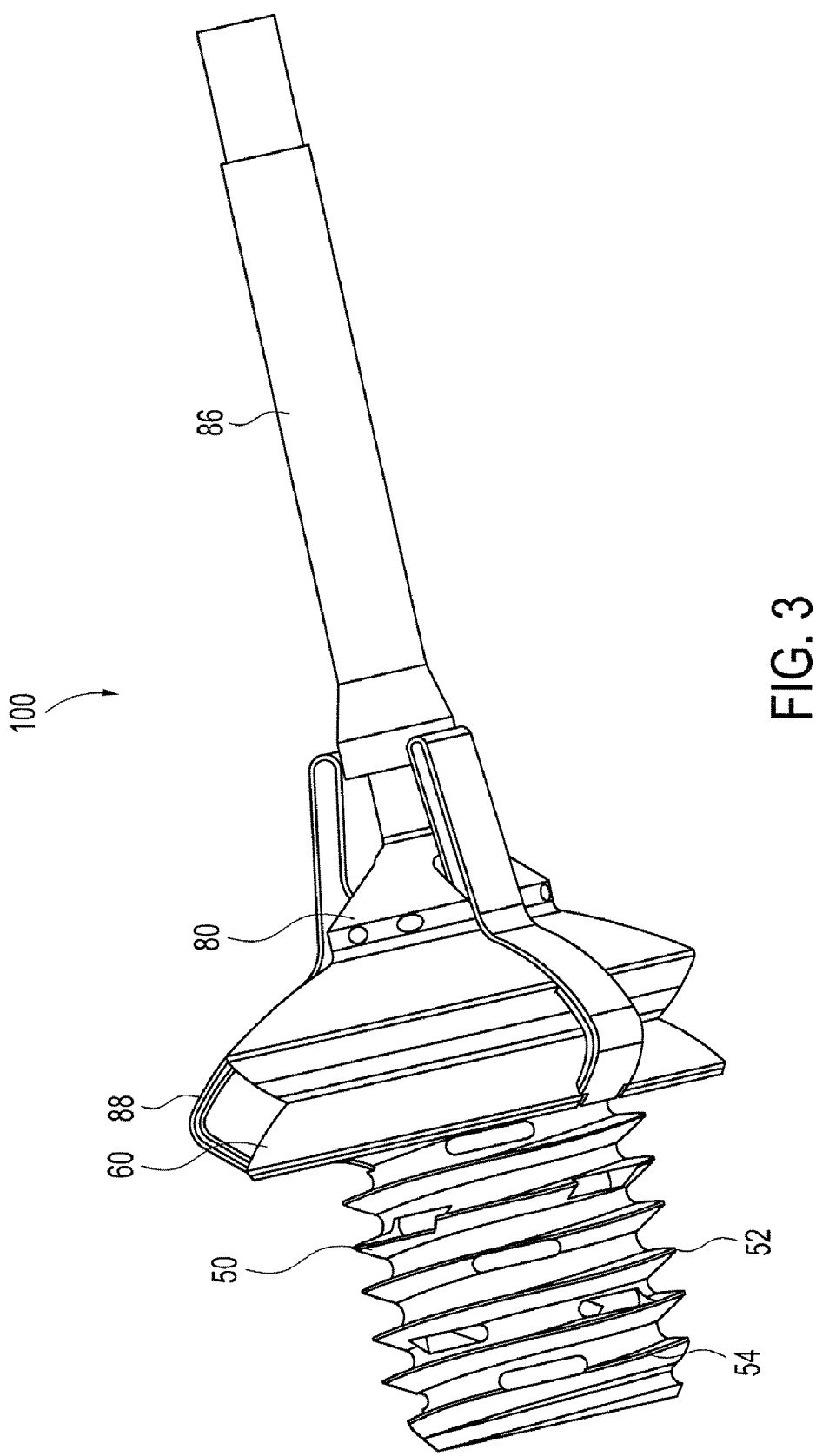
FIG. 3 is a schematic view of the implant/inserter assembly of the present invention.
Figure 4A:
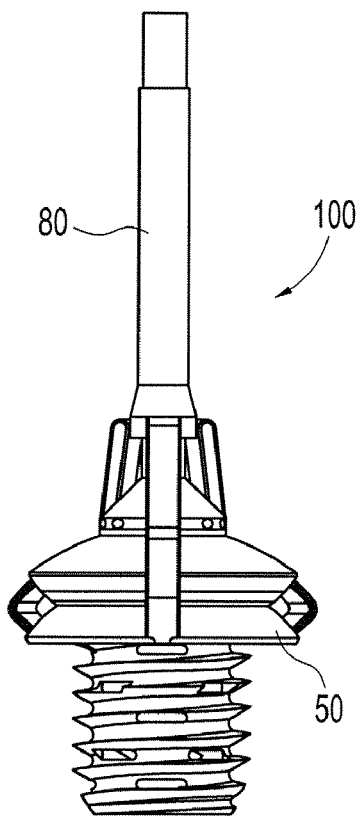
FIGS. 4(a)-(c) illustrate additional perspective views the implant/inserter assembly of the present invention.
Figure 4B:
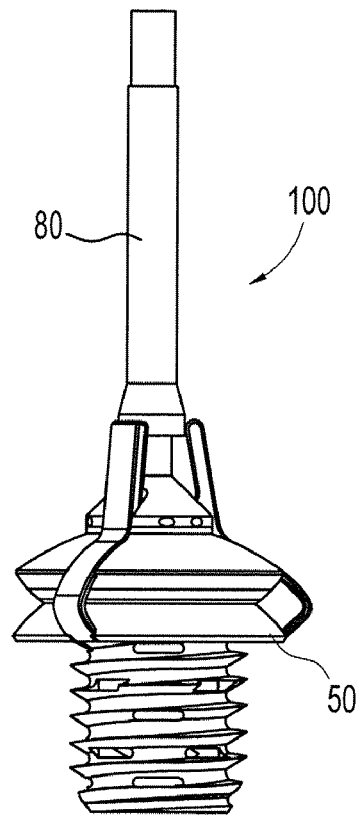
Figure 4C:
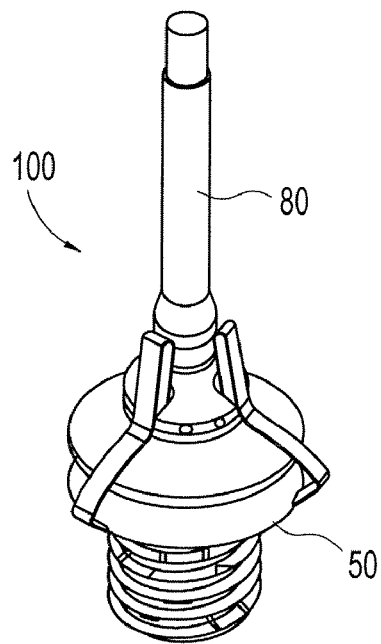

As shown in the drawings, implant/inserter assembly 100 comprises an implant or implant screw 50 designed to be securely engaged by an inserter or driver 80. FIG. 1 illustrates the detached configuration of the implant/inserter assembly 100 (i.e., implant 50 detached from inserter 80). FIGS. 2-4 illustrate the attached configuration of the implant/inserter assembly 100 (i.e., implant 50 engaged by inserter 80).

The implant screw 50 is preferably formed of titanium or titanium alloy materials, for example, or other biomedically acceptable materials. Alternatively, the implant screw 50 can be formed of a bioabsorbable, biocompatible material, such as Resomer L210 Poly (L-Lactide) acid (PLLA) or an equivalent material. In addition to being biocompatible and bioabsorbable, a dome shaped implant formed of PLLA material provides the advantages of not being visible on radiographs and not interfering with MRI or CT scans.

Figure 5:
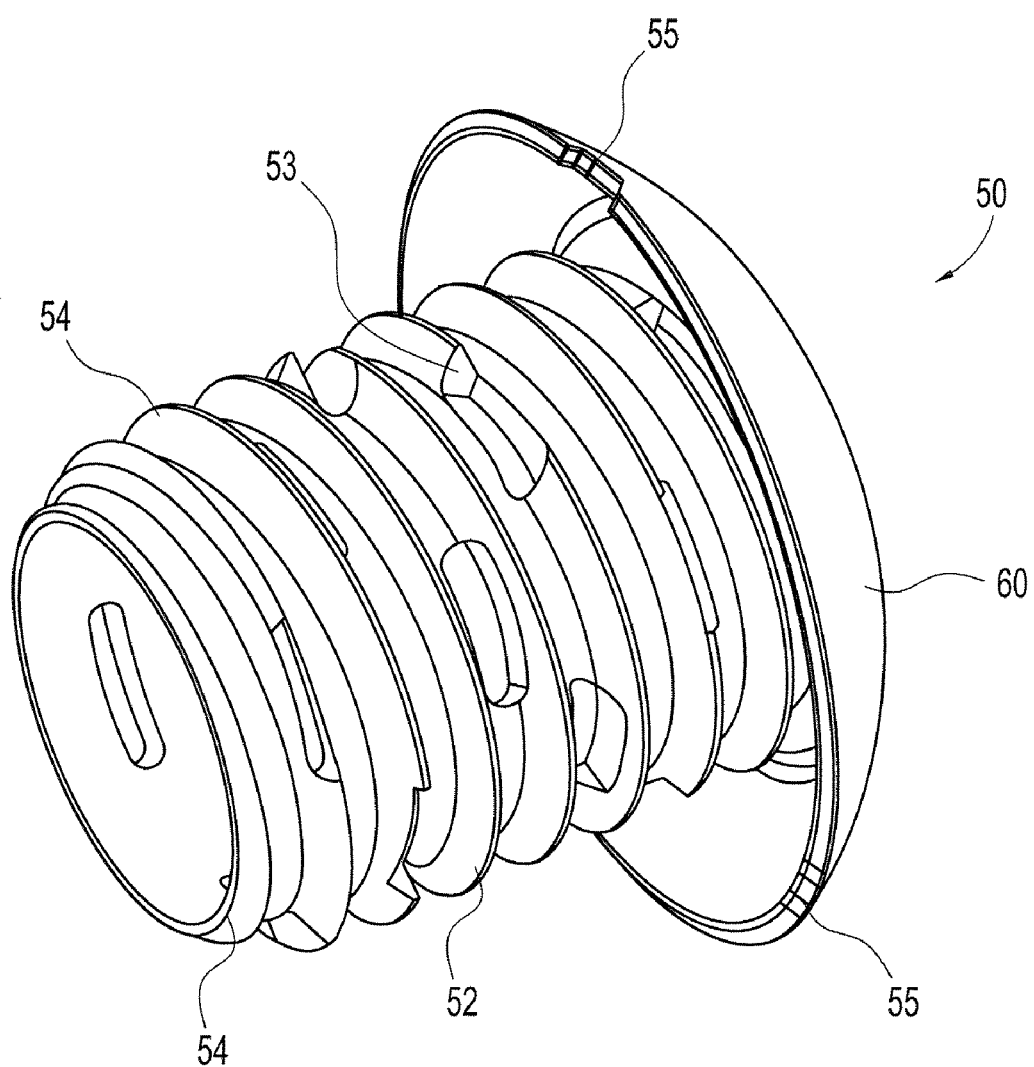
FIG. 5 is a perspective view of the implant of the present invention.
Figure 6:
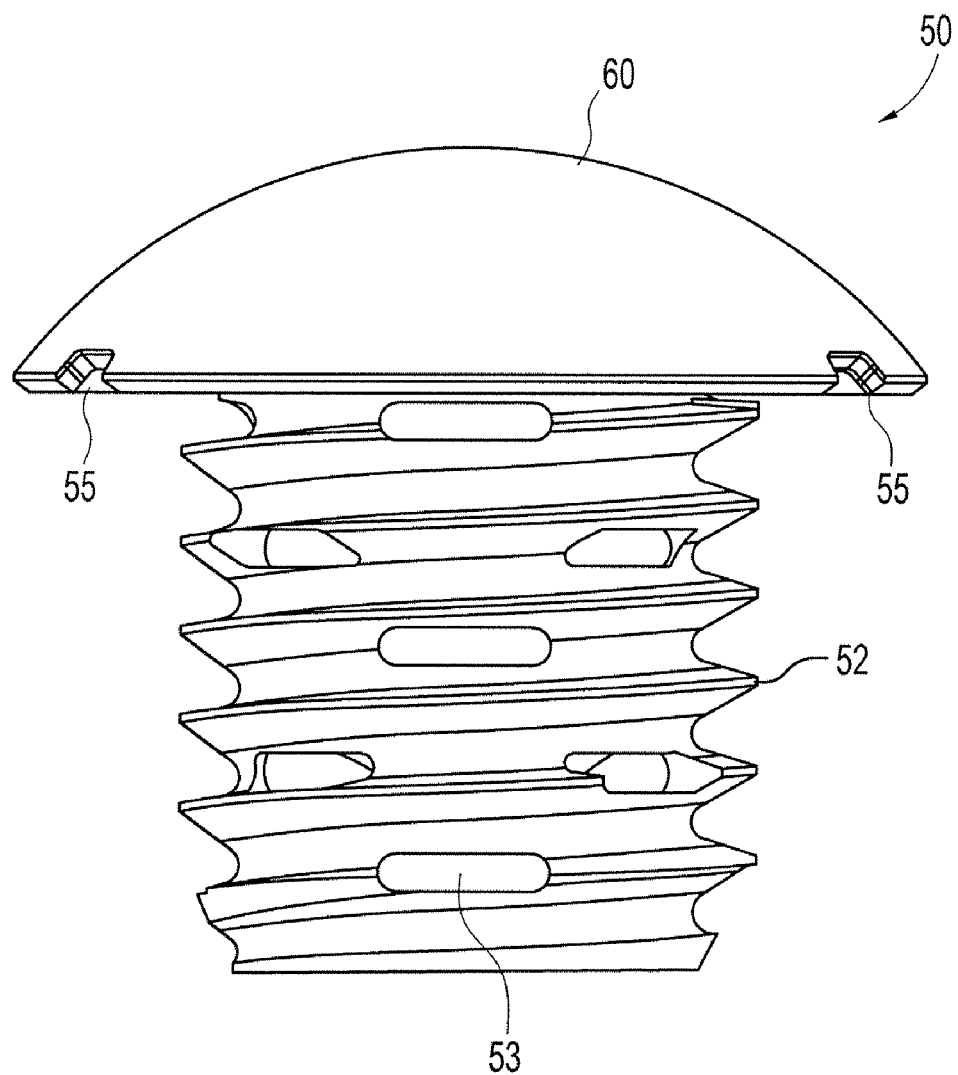
FIG. 6 is a front view of the implant of the present invention.
Figure 7:
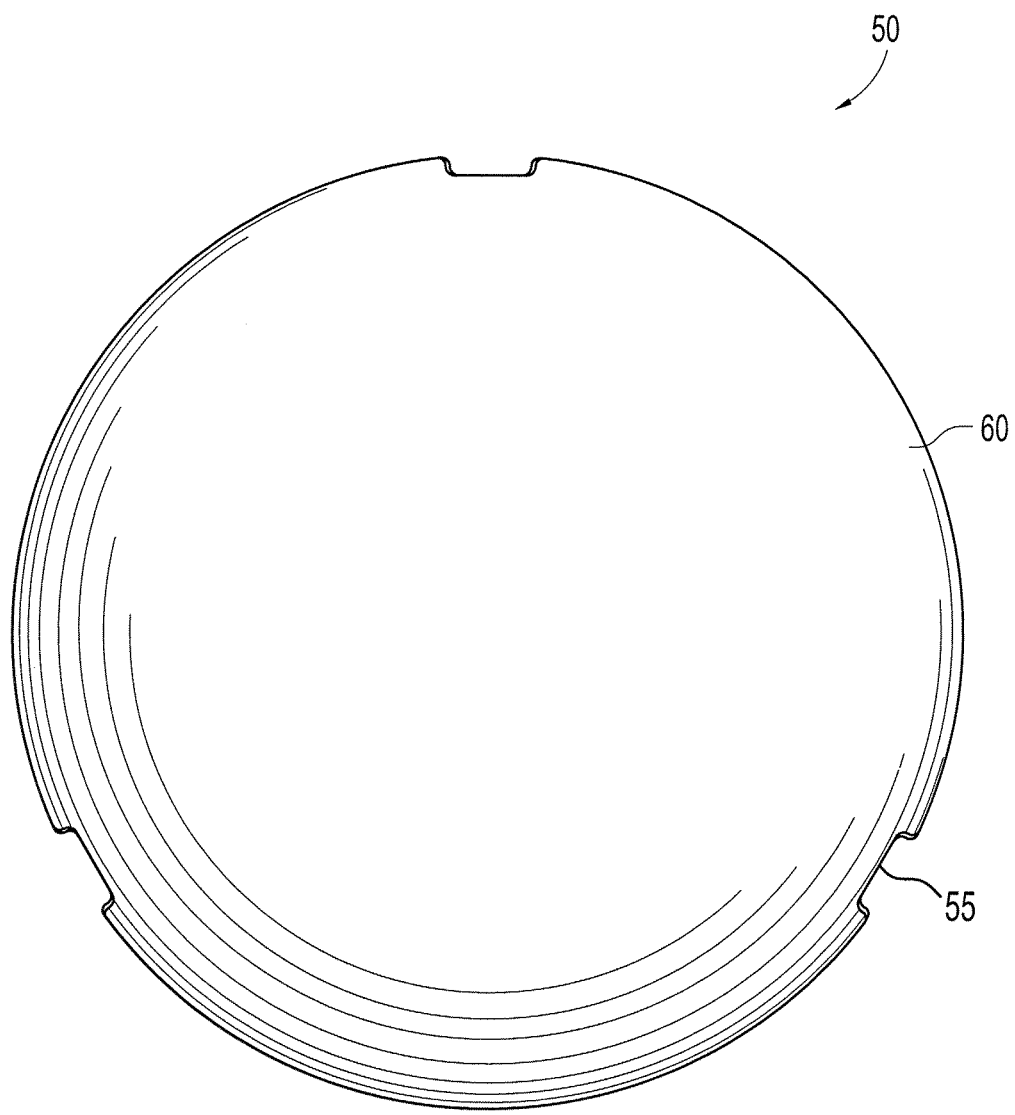
FIG. 7 is a top view of the implant of the present invention.
Figure 8:
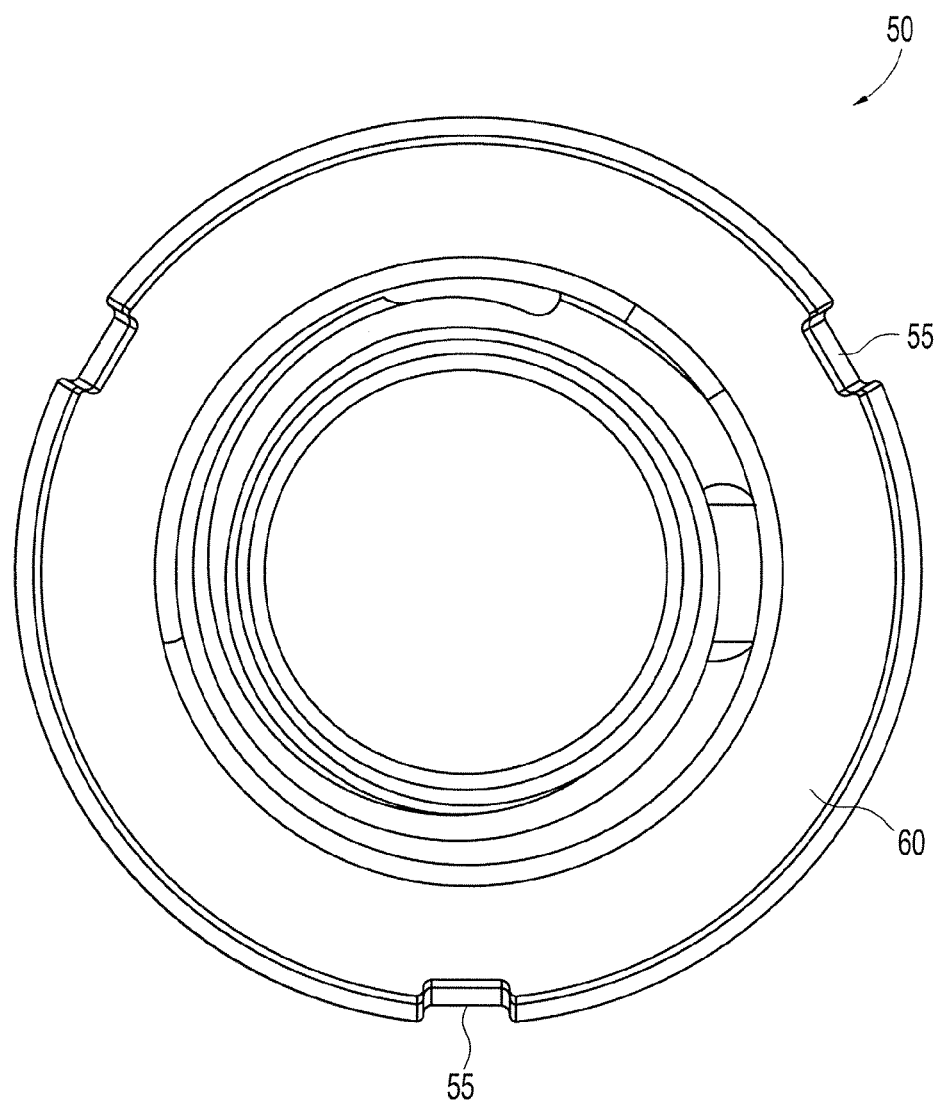
FIG. 8 is a bottom view of the implant of the present invention.

In a preferred embodiment, and as illustrated in FIGS. 5-8, implant 50 is provided with a body 52 and a dome or eclipse-like head 60. Body 52 may be provided with a continuous thread 54 (as shown in the drawings) and may have a cylindrical configuration with a blunt end at its distal end 56. In exemplary embodiments, body 52 may be partially threaded. As shown in FIGS. 5 and 6, for example, body 52 may be also provided with a plurality of fenestrations 53, to allow tissue in-growth.

The proximal face of the head 60 has at least one opening or indent 55 (FIGS. 5-8) for engaging an inserter or driver. Although many different drive coupling arrangements are possible, the preferred embodiment of the invention has three equally spaced openings or arcuate slots 55 formed in the dome-shaped head to engage the driver/inserter used for delivery and installation of the implant, as described below. Preferably, the plurality of indents or slots 55 are provided on the periphery or edge of the head 60. The plurality of indents or slots 55 may have various configurations and geometries, for example, a rectangular shape as illustrated in FIGS. 5-8. However, indents 55 may have any configuration that allows them to be engaged by arms (or tabs) 88 (FIGS. 1-3) of the corresponding inserter instrument 80. Slots 55 are positioned on the edge of head 60 so that the depth of slots 55 can extend slightly below the depth of head 60. In this manner, slots 55 enable solid coupling between an engaged inserter/driver and the screw for inserting/driving the screw.

As also illustrated in FIGS. 1-4, inserter 80 is preferably provided with handle 85, shaft 86 and plurality of arms 88. Arms 88 may be provided in any number and configuration to allow to securably engage indents 55 on the periphery or edge of the implant 50.

In use, and according to an exemplary embodiment only, the arms 88 of the inserter 80 attach to the indents or slots 55 of the implant 50 by sliding back shaft 86 of the inserter 80. Alternatively, the arms 88 of the inserter 80 detach from the indents or slots 55 of the implant 50 by sliding shaft 86 forward (with open arms). Engagement and/or disengagement of the arms 88 with/from the indents 55 may be facilitated by actuating an actuating mechanism (for example, a knurl or a ring feature) provided on, or in communication with, the handle 85 of the inserter 80. The actuating mechanism (for example, the knurl or the ring feature) is configured to slide back or forth the shaft 86 of the inserter 80.

The present invention also provides a method of conducting arthroscopic surgery by: (i) forming a socket at a surgical repair site; (ii) providing the implant/inserter assembly 100 of the present invention in the vicinity of the surgical repair site; and (iii) securing the implant at least partially (preferably fully) within the socket.

The implant screw and driver assembly of the present invention are designed to be used to insert a dome shaped implant within a joint capsule, for example, the knee capsule or the shoulder joint, to resurface the load bearing surface of the joint. However, it will be apparent to those skilled in the art that the present invention has a variety of possible uses and applications relating to screw insertion, not necessarily limited to joint surgery or to orthopedics.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed is:

1. A method for joint resurfacing, comprising the steps of:
providing an implant in the vicinity of an arthroscopic site, the implant comprising a distal end, a body portion of a first diameter and a proximal end, wherein the proximal end is provided with a dome-shaped head of a second diameter which is greater than the first diameter, and wherein the dome-shaped head is provided with a plurality of indentations disposed on a periphery of an outer surface of the dome-shaped head;
providing a driver in the vicinity of the implant, the driver comprising a handle, a shaft, and a plurality of arms that extend around the dome-shaped head of the implant and are configured to securely engage the plurality of indentations on the periphery of the outer surface of the dome-shaped head of the implant;
engaging the implant with the driver to obtain a driver/implant screw assembly; and
securing the implant at the arthroscopic site.

2. The method of claim 1, wherein the implant screw comprises titanium or titanium alloy.

3. The method of claim 1, wherein the implant is a bioabsorbable screw.

4. The method of claim 1, wherein the act of engaging the implant comprises moving the shaft of the driver so that the plurality of arms securely engage the plurality of indentations on the outer surface of the head.

5. The method of claim 1, wherein the arthroscopic site is a joint in the knee, shoulder, hip, ankle, elbow, hand or foot.

* * * * *